United States Patent [19]

Beisang et al.

[11] Patent Number: 4,950,282
[45] Date of Patent: Aug. 21, 1990

[54] WOUND CLOSURE STRIPS

[75] Inventors: Arthur A. Beisang, Roseville; Daniel G. Holman, Blaine, both of Minn.; Robert A. Ersek, Austin, Tex.

[73] Assignee: Genetic Laboratories, Inc., St. Paul, Minn.

[21] Appl. No.: 295,937

[22] Filed: Jan. 11, 1989

Related U.S. Application Data

[63] Continuation of Ser. No. 812, Jan. 6, 1987, abandoned, which is a continuation of Ser. No. 663,482, Oct. 22, 1984, abandoned.

[51] Int. Cl.$^5$ ............................................. A61B 17/04
[52] U.S. Cl. .................................................. 606/216
[58] Field of Search ............ 128/335, 155, 327, 335.5, 128/171, 156, 157; 606/215, 216

[56] References Cited

U.S. PATENT DOCUMENTS

| | | | |
|---|---|---|---|
| 1,230,444 | 6/1917 | Teed | 128/335 |
| 2,018,517 | 10/1935 | Fetter | 128/335 |
| 2,711,739 | 6/1955 | Fishbein | 128/335 |
| 2,740,403 | 4/1956 | Schueler | 128/156 |
| 2,751,909 | 6/1956 | Weitzner | 128/335 |
| 2,798,492 | 7/1957 | Baines et al. | 128/335 |
| 3,402,716 | 9/1968 | Baxter | 128/155 |
| 3,698,395 | 10/1972 | Hasson | 128/155 |
| 4,222,383 | 9/1980 | Schossow | 128/335 |
| 4,370,981 | 2/1983 | Sanderson | 128/335 |
| 4,513,739 | 4/1985 | Johns | 128/156 |

FOREIGN PATENT DOCUMENTS

| | | | |
|---|---|---|---|
| 304989 | 9/1915 | Fed. Rep. of Germany | 128/335 |
| 321649 | 11/1929 | United Kingdom | 128/335 |

Primary Examiner—Theatrice Brown
Attorney, Agent, or Firm—Orrin M. Haugen; Thomas J. Nikolai; Frederick W. Niebuhr

[57] ABSTRACT

An adhesive strip-like bandage for application to skin wounds for sealing the wound without surface stitches or staples. The wound closure strips may be fabricated from a bias cut, woven, or non-woven, polymer-based material or other film, exhibiting uni-directional stretch properties which permits the strips to stretch in a controlled manner during wound healing. The strip bandages are detachably mounted to a backing member and in one configuration comprise a comb-like structure.

6 Claims, 1 Drawing Sheet

WOUND CLOSURE STRIPS

This is a Continuation of application Ser. No. 07/000,812, filed Jan. 6, 1987 (abandoned), which is a Continuation of application Ser. No. 06/663,482, filed Oct. 22, 1984, now abandoned.

BACKGROUND OF THE INVENTION

The present invention relates to medical bandaging and, in particular, to an improved stretchable woven or nonwoven polymer wound closure strip exhibiting a high degree of dynamic adhesion.

Wounds closure strips, along with staples and various other mechanical fasteners have recently become acceptable alternatives for sewn stitches in closing many types of skin wounds. Wound closure adhesive bandages are in many respects more desirable than stitches in that they facilitate wound healing by adhesively binding the underlying portions of the wound in direct contact with a flush skin surface. Hence, upon healing, scar tissue is minimized, especially scar tissue that would otherwise show the stitch marks and/or closure line.

While wound closure strips may take various forms and be fabricated in a variety of shapes, they typically comprise a sterile piece of adhesive backed tape of a suitable length that upon mounting over the wound, acts to hold the exposed wound closed. One commonly known and pre-existing form of this bandaging comprises a butterfly bandage wherein the bandage is configured in the general shape of a butterfly. That is, it has a pair of relatively large surface area adhesive portions connected by a relatively narrow section (much like the shape of an hour glass or butterfly) and which narrow portion is placed over a closed wound, while the larger portions maintain the wound surfaces in contact.

Typically, the material previously employed in such bandaging has included a plurality of lengthwise fiberglass strands supported in a paper-like carrier or backing. The strands provide rigidity of the bandaging. Such tape and fiber glass strands are also configured to "breathe". A drawback to the use of fiberglass strands in the paper-like tape, however, has been that the bandaging is not permitted to move or stretch along the direction of the fiberglass strands as pressure is placed on the wound by the patient during normal activities. Thus, with normal movement, the wound closure strip on opposite sides of the wound tend to stretch the skin with resulting mechanical damage to the skin at the extreme ends of the bandage or release of the wound closure strip from the skin. Further, when left in place for some time, the backing material deteriorates and upon removing such wound closure strips, the individual fiberglass strands do not lift off as a unit from the skin, and oftentimes it is required that a medical attendant separately pick each strand of fiber from the skin using forceps, upon removal of the wound closure strip.

It is with the foregoing problems in mind that the present invention was designed and developed as an improvement to permit the stretching of the wound closure strip with the skin movement and to prevent the leaving of a bandage residue, upon wound closure strip removal. The wound closure strip must exhibit a porosity great enough to allow for a movement of exudates through the strip without causing release of the wound closure strip from the skin. Specifically, these ends are achieved in the present invention via the fabrication of the present wound closure strips from a woven or nonwoven, polymer based material which is designed to exhibit a stress, strain modulus compatible with that of the underlying skin. Since the intent is to produce a thin closure relative to its width for optimum flexibility and this goal is to be a function of the planar stretch characteristic of the underlying skin, this property can be defined as follows:

$E_t$(Young's Modulus is irrespective of thickness)=Stress/Strain, where stress is defined as the load divided by the unit width, and strain is defined as the change in unit length divided by the gauge length. More particularly, it is desired to have a modulus higher than, or at least equal to, that of the underlying skin to provide some reinforcement to the skin and to allow for the fact that the closure strips cover only a part of the wound length. If the modulus $E_t$, is expressed in pounds per inch, a useful range as far as the application to wound closure strips is concerned has been found to be from 0.5 to 110.

The material is further fabricated to permit the bandage to breathe and the material is such that upon bandage removal, it does not separate to leave undesired residue. When forming the present wound closure strip, this material is cut at a predetermined bias angle to provide the desired modulus $E_t$. This provides the individual strips with a property of "dynamic adherence" that permits the bandage to stretch along with the skin, thereby reducing mechanical damage to the skin or release of the wound closure strip from the skin during movement or swelling of the skin.

A further embodiment of the invention involves the degree of permanence of the elastic properties of the bandage material. Medical experience has shown that a very high modulus bandage material can cause skin damage and wound closure release because of its underlying nature. It is no less true, however, that a low modulus material with good elastic recovery can also cause a degree of the same distress depending upon the extent of the appliation pre-load. It would be inconvenient to require the medical practitioner to limit the extent of the load he or she applies to the bandage strip when mounting it over the wound. It is, therefore, important that the wound closure material not only have low elastic modulus, but also poor elastic recovery. Thus, a material with a stress, strain modulus within the above desired range would be unacceptable if it also possessed an elastic recovery equal to or above the range of commercially available urethane film bandages such as the Smith Nephew Company's Opsite ™, the 3M Company's Tegaderm ™ and Johnson & Johnson's Bioclosure ™.

A bandage material elastic modulus, $E_t$, compatible with that of human skin provides required support over the wound area. The stress relaxation characteristic referred to as a high tension set or poor elastic recovery provides a comfortable complianace during the period of healing. Together, these properties provide "dynamic adherence" of the wound closure strip.

The above objects, advantages and distinctions of the present invention will become apparent, however, upon reference to the following description and to the appended drawings. Before referring thereto, though, it is to be recognized that the following description is made with respect to the presently preferred embodiment only and that various modifications may be made thereto such as in the ultimate shape of the bandage, its stress/strain modulus, etc.

SUMMARY OF THE INVENTION

If medical wound closure strips are formed from a woven or non-woven polymer-based, breathable material exhibiting uni-directional stretch properties, the material may be cut on a bias to the stretch axis of the material such that the resulting wound closure strip exhibits the desired modulus which permits it to be compatible with skin movement. This prevents wound closure strip release and attendant mechanical damage of skin, while still maintaining approximation of wound edges.

In one embodiment of the invention, individual parallel strips are die cut from the uni-stretch material and detachably mounted to a slit backing member. In a second embodiment, the bandaging is cut in a comb-like configuration, with each of a plurality of individual elongated portions being coupled to a backing strip portion and ultimately to a detachable slit member.

DESCRIPTION OF THE PREFERRED EMBODIMENT

Figure 1:
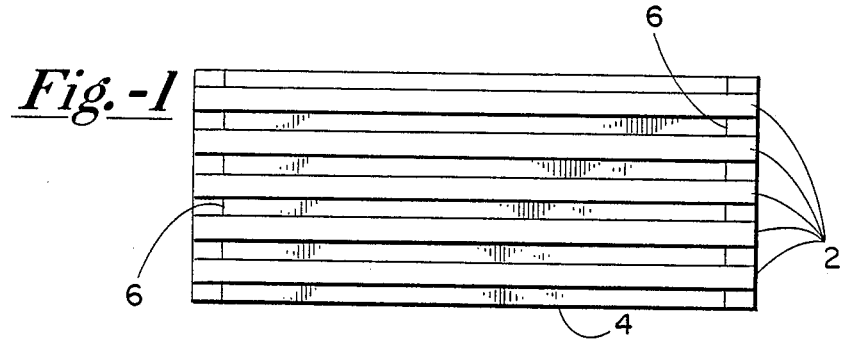
FIG. 1 shows a plurality of detachably mounted wound closure strips.

Referring to FIGS. 1, a view is shown of a pluality of the present wound closure strips 2 as they appear, upon being mounted to a slit backing member 4. Specifically, a plurality of parallel mounted wound closure strips 2 are adhesively mounted to the backing member 4 which has been slit longitudinally along the slit lines 6 at the lateral ends of the member 4 for facilitating individual strip removal, That is, upon bending and twisting the slit ends of the backing member, the strips 2 may be individually removed from the backing member 4 and applied to a open wound.

In that regard, the strips 2 may be used in conjunction with a number of surgical procedures and/or as emergency bandaging for closing open wounds, in lieu of the use of individual sewn stitching. Before applying the strips 2, and assuming that the wound has been properly cleaned and disinfected, individual sections of the wound are drawn together by hand and over the wound, appropriate lengths of the strips 2 are positioned in spaced apart relation. Upon releasing the wound, the adhesive ends of the strips on each side of the wound bind the edges of the wound together. By using a plurality of strips extending normal to the wound line, the wound edges can be completely drawn together. By maintaining tissue contact between the opposite sides of the wound, the wound is thus permitted to heal without forming a ridge of scar tissue along the wound line and also without scar tissue that would otherwise result from the individual stitches.

Figure 2:
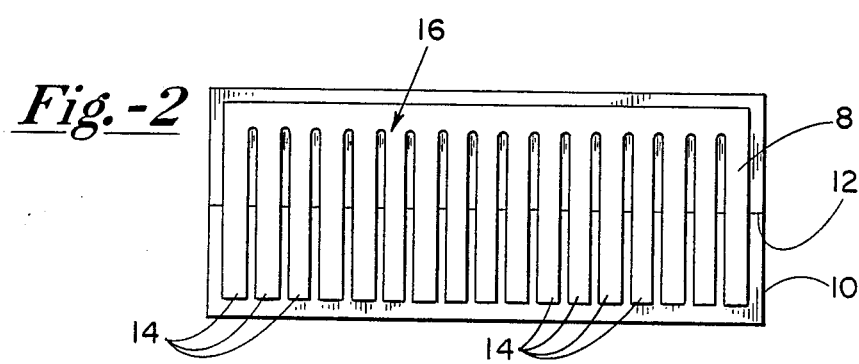
FIG. 2 shows a comb-like wound closure bandage.

Referring next to FIG. 2, yet another configuration of wound closure strips is shown. It comprises a comb-like structure 8 that is detachably mounted to a backing member 10 that has been slit lengthwise along a slit 12 to facilitate wound closure strip application. With the comb-like configuration of FIG. 2, the wound closure strip 8 may thus be removed as a unitary structure and each of the longitudinal strip sections 14 can be maintained in a predetermined spaced relation to each other via the lengthwise backing portion 16. Alternatively, the backing member 10 and/or backing portion 16 may be cut at an appropriate point so as to provide the attending physician with a number of strip sections 14 to secure the wound. For relatively long wounds, a number of bandages 8 may be placed over sections of the wound to seal the wound. The backing material is designed so that upon removal of a portion of the back, the wound is visualized so that the opposing edges can be properly aligned to effectuate a minimum of scar tissue.

As mentioned, the present wound closure strips 2 and 8 possess a number of desirable properties over prior art wound closure strips in that they accommodate skin stretching and facilitate removal from the patient and do not leave bandaging residue, upon removal. These ends are achieved in the present wound closure strip via the employment of a woven or non-woven polymer or plastic wound closure strip material that is purchased in rolls of a desired width from a number of manufacturers. A suitable acrylic, skin compatible adhesive is deposited over one surface of this bandaging material.

Figure 3:
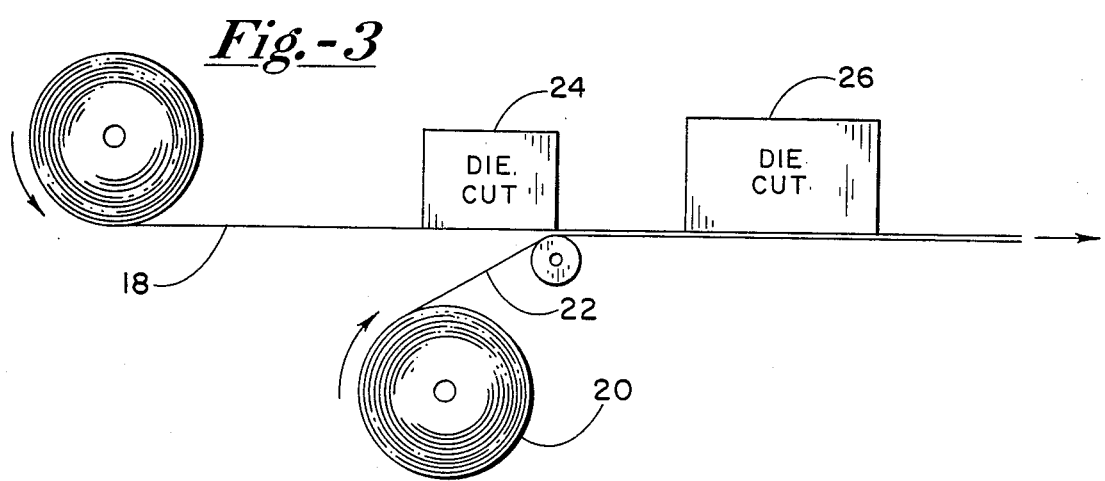
FIG. 3 shows a representative schematic diagram of the process by which the present wound closure strips are fabricated.

Turning attention now to FIG. 3, upon receipt of the rolls of adhesive bond wound closure strip material and during conversion process, a web of wound closure strip material 18 is caused to pass in overlying relation to a roll of split backing material 20 and from which a web of release material 22 is caused to be brought into contact with the bandaging material 18 after it is cut into a desired shape. Just prior to the overlap of the webs 18 and 20, a die cutting fixture 24 sequentially acts to cause a die assembly formed with an appropriate wound closure strip configuration to stamp corresponding segments from the web 18 relative to a lower lying hard platten as the web 18 passes and which stamped wound closure strips are then caused to be deposited on the web of release material 22.

Figure 4:
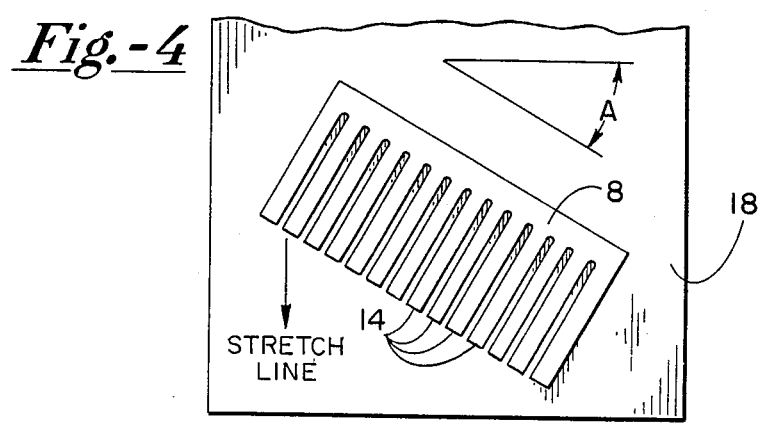
FIG. 4 shows a representative top view of a web of uni-stretch material relative to a die cut comb-like bandage.

Turning attention now to FIG. 4, as the web of wound closure material 8 passes the die cutting station 24, its easy stretch axis or axis of lowest modulus, is typically oriented in orthogonal relation thereto while the die cut assembly 24 is positioned at a predetermined bias angle "A" so as to cause individual wound closure strips to be die cut with predesigned modulus for each of the strip members 2 or 14. A maximum stretchability is obtained by placing the strip members 2 and 14 parallel to the easy stretch axis and a minimum stretch is obtained by placing each of the members 2 and 14 orthogonal thereto, i.e., aligned with the hard stretch axis where the modulus is greatest. If wooven or non-woven materials have the desired modulus, there is no need for a bias cut. Thus, upon positioning the bandage strips 2 and 14 over the wound, the bandage is able to stretch with the underlying skin, while maintaining wound closure. The stretch in the tape must be sufficient to obviate stress at the ends of the adhesive wound closure strip which presently results in abrasions and skin irritations called tape burns. By varying the bias angle "A", the modulus of the resulting strips can be tailored so that the proper yield/compliance in the strip members may be obtained.

For most purposes, it has proved to be desirable to fabricate the strips so that they exhibit a modulus, $E_t$, in the range of 0.5 pounds per inch to 110 pounds per inch.

When so fabricated, the strips provide sufficient holding force to maintain the edges of the wound in abutment, but enough "give" to avoid mechanical skin damage. The stress relation or elastic recovery must be less than commercially available urethane bandages, such as the ones produced by the Smith Nephew Company, 3M Corporation, or Johnson & Johnson, Inc. and sold under the trademarks previously mentioned. Conversely, the tension set of the strips must be relatively high compared to that of the commercially available urethane bandages.

Returning attention to FIG. 3, once the individual bandages are die cut, each is deposited on an underlying web of the backing member release material 22 and caused to pass beneath a second die cutting station 26. There, the backing member material 22 is slit to form the slit lines 6 or 12 and die cut to the ultimate shape of the backing member 4 or 10 relative to the die cut bandage. The individually mounted bandages may then be sterilized and packaged in conventional fashion for use in the above-described manner.

While the present invention has been described with respect to its presently preferred embodiment and, in particular, to two embodiments thereof, it is to be recognized that various modifications may be made thereto by those of skill in the art without departing from the spirit and scope hereof. It is accordingly contemplated that the following claims should be interpreted so as to include equivalent embodiments within the spirit and scope thereof.

What is claimed is:

1. A wound closure strip comprising:

an elongate imperforated pad member formed from a polymeric material of a density to permit the pad member to breathe and expose the wound to ambient air, said pad member being constructed of a material having an easy stretch axis and a hard stretch axis orthogonal to the easy stretch axis, thus exhibiting uni-directional stretch properties said pad member being cut from said material such that its longitudinal axis is oriented at a predetermined oblique angle relative to both said axis of said material such that the pad member has modulus of elasticity ($E_t$) irrespective of thickness, in the range of 0.5 to 110 pounds per inch, said material having a low elastic recovery characteristic; and adhesive means bonded to at least one surface of said pad member for adhering said pad member to human skin.

2. A wound closure strip as in claim 1 and further including a backing member upon which said adhesively coated pad member is detachably mounted.

3. A wound closure strip as set forth in claim 1 wherein said adhesive is a low allergenic material.

4. A wound closure strip as set forth in claim 3 wherein said low allergenic material is an acrylic-based adhesive.

5. A wound closure strip as set forth in claim 1 wherein said pad member is configured on said backing member as a plurality axially spaced apart parallel lengthwise strips.

6. A wound closure strip as set forth in claim 1 wherein said pad member comprises a lengthwise portion from which a plurality of strip portions extend in a parallel axially spaced apart relation, each of said strip portions being orthogonal to said lengthwise portion.

* * * * *